United States Patent
Summers

[19]

[11] Patent Number: 5,837,207
[45] Date of Patent: Nov. 17, 1998

[54] PORTABLE GERMICIDAL AIR FILTER

[75] Inventor: George Robert Summers, Carleton Place, Canada

[73] Assignee: Engineering Dynamics Limited, Ontario, Canada

[21] Appl. No.: 841,900

[22] Filed: Apr. 17, 1997

[51] Int. Cl.[6] ................................ A61L 9/00; A61L 9/20
[52] U.S. Cl. .................... 422/121; 422/122; 250/504 R; 55/279; 96/16
[58] Field of Search .................................. 422/121, 122; 55/279, 276; 96/16, 96; 250/455.11, 492.1, 504 R

[56] References Cited

U.S. PATENT DOCUMENTS

| 2,248,618 | 7/1941 | Fischer ........................................ 250/52 |
| 2,628,083 | 2/1953 | Rense .......................................... 261/14 |
| 3,518,046 | 6/1970 | Cicirello ....................................... 21/53 |
| 3,576,593 | 4/1971 | Cicirello ....................................... 21/53 |
| 3,757,495 | 9/1973 | Sievers ....................................... 55/279 |
| 3,798,879 | 3/1974 | Schmidt-Burbach et al. ............. 55/102 |
| 4,017,736 | 4/1977 | Ross .......................................... 250/435 |
| 4,019,062 | 4/1977 | Rongren ................................. 250/492 R |
| 4,025,795 | 5/1977 | Lackore et al. ........................... 250/504 |
| 4,694,179 | 9/1987 | Lew et al. ................................. 250/431 |
| 4,750,917 | 6/1988 | Fujii ............................................... 55/6 |
| 4,806,768 | 2/1989 | Keutenedjian ........................... 250/436 |
| 5,330,722 | 7/1994 | Pick et al. ................................. 422/121 |
| 5,681,145 | 10/1997 | Neely et al. ............................. 416/203 |

*Primary Examiner*—Krisanne Thornton
*Assistant Examiner*—Fariborz Moazzam
*Attorney, Agent, or Firm*—Hardaway Law Firm, P.A.

[57] ABSTRACT

A lightweight portable germicidal air filter for home and personal use is disclosed. The air filter includes a cabinet which houses an electrostatic air filter, an ultraviolet lamp and a parabolic reflector or a convex lens for focusing the ultraviolet radiation emitted by the lamp on an upstream side of the air filter. The reflector or the lens are constantly oscillated to systematically sweep the upstream side of the filter with germicidal levels of radiation. A fan located adjacent the downstream side of the filter draws air through the filter and impels it out through areas for air outlet in the sidewalls of the cabinet. The advantage is a simple, lightweight germicidal air filter with few moving parts which is inexpensive to manufacture.

24 Claims, 5 Drawing Sheets

PORTABLE GERMICIDAL AIR FILTER

TECHNICAL FIELD

The present invention relates to the removal of suspended particulate matter from air and, in particular to the removal of particulate matter from air by filtration and the destruction of microorganisms in the particulate matter removed.

BACKGROUND OF THE INVENTION

The airborne transmission of disease organisms, especially respiratory disease organisms, has long been recognized as a serious problem. Health care authorities and aerobiologists have now become acutely aware of the problem due to the evolution of antibiotic resistant strains of streptococcus and tuberculosis, for example. Although, the airborne transmission of disease is not well understood, it is abundantly clear that many diseases caused by both bacteria and viruses are primarily transmitted from host to host by air currents. It is also known that certain infectious agents such as tuberculosis bacteria can survive many hours suspended in air. Quarantining individuals infected with resistant strains of tuberculosis is therefore at best only a partial solution, since the air they pollute must eventually circulate into space occupied by uninfected individuals unless the air is treated to remove and destroy the resistant bacteria. To this end, germicidal air filters have been invented. Examples of such filters are described in U.S. Pat. No. 5,330,722 which issued on Jul. 19, 1994 to W. E. Pick and has subsequently been assigned to the applicant. While the germicidal air filtration systems described in that patent have proven to be very effective in removing microorganisms from the air and destroying them, the air filtration systems described are principally adapted to permanent or semi-permanent installations and are not primarily adapted to lightweight portable filters intended for home and/or personal use.

Another recently recognized hazard of modern living is the dust mite. Modern dwellings with their air-tight closures, central heating and cooling systems, abundant carpeting and minimal through flow of outside air provide ideal breeding grounds for dust mites. These mites are nearly microscopic and readily become airborne. Airborne mites are of course inhaled, which can cause strong allergic reactions in some individuals and contributes to the discomfort of all. With proper filtration equipment, especially in sleeping areas, dust mites can be removed from the air and destroyed, thus limiting exposure to airborne mites, curbing population growth and controlling infestations. A germicidal air filter unit in a sleeping area can contribute to the control of dust mites.

It is therefore an object of the invention to provide a lightweight germicidal air filter which is portable and adapted for home and/or personal use.

It is a further object of the invention to provide a germicidal air filter which requires a minimum number of moving parts.

It is yet a further object of the invention to provide a lightweight germicidal air filter which is simple to construct and inexpensive to manufacture.

SUMMARY OF THE INVENTION

These and other objects of the invention are realized in a germicidal air filter comprising a stationary filter medium for removing particulate matter including at least a portion of microorganisms from an air stream to be filtered, the filter medium having an upstream side exposed to the air to be filtered;

at least one ultraviolet radiation source located in proximity of the upstream side of the filter medium for exposing at least a portion of that side of the filter medium to ultraviolet radiation;

means for focusing the ultraviolet radiation emitted by the source so that a predefined area of the upstream side of the filter medium is exposed to the focused ultraviolet radiation at any given time; and means for oscillating the means for focusing the ultraviolet radiation so that a surface of the upstream side of the filter medium is systematically exposed to germicidal levels of radiation.

The germicidal air filter in accordance with the invention preferably comprises a cabinet having an air intake area and an air discharge area with a filter medium disposed between the air intake area and the air discharge area so that substantially all air drawn through the cabinet passes through the filter medium. The filter medium is preferably a planar filter and most preferably an electrostatically enhanced planar filter of a type described, for instance, in U.S. Pat. Nos. 4,978,372 and 4,886,526 which issued on Dec. 18, 1990 and Dec. 12, 1989, respectively. Air is preferably moved through the cabinet by a fan located adjacent the downstream side of the filter medium. An ultraviolet radiation source is located adjacent an upstream side of the filter medium. The ultraviolet radiation source is preferably an ultraviolet lamp that is stationarily mounted in proximity to the upstream side of the filter medium. In order to ensure that substantially the entire surface of the filter medium is exposed to levels of radiation which are lethal to known microorganisms, it is preferable that a means for focusing the radiation emitted by the ultraviolet source be provided so that the radiation is focused onto a predefined area of the filter surface, and that the means for focusing the ultraviolet radiation be oscillated about the ultraviolet source so that substantially all of the filter surface is systematically irradiated with an intensity level of radiation which is lethal to known microorganisms. The focusing of the ultraviolet radiation may be accomplished by a parabolic reflector positioned behind the bulb or a reflector in combination with an elongated lens positioned in front of the bulb so that substantially all of the ultraviolet radiation emitted by the ultraviolet source is focused in a relatively narrow, elongated band on the upstream side of the filter surface. The means for focusing the radiation, e.g. a reflector or the elongated lens, are oscillated about an axis parallel to the axis of the radiation source by an electric motor, for example, which drives a cam shaft assembly at a predefined rate to effect the desired irradiation of the upstream side of the filter medium. It has been found that preferably the motor rotates the cam shaft assembly at about 2 rpm, which yields a sweep of the filter surface each 30 seconds, although other rates of oscillation may prove equally effective. Since the germicidal air filter in accordance with the invention includes very few components and the components are light in weight, it is possible to provide a germicidal air filter which is easily handled and may be used in home and/or personal applications such as in the workplace.

BRIEF DESCRIPTION OF THE DRAWINGS

The invention will now be further explained by way of example only and with reference to the following drawings wherein.

DETAILED DESCRIPTION OF THE INVENTION

Figure 1:
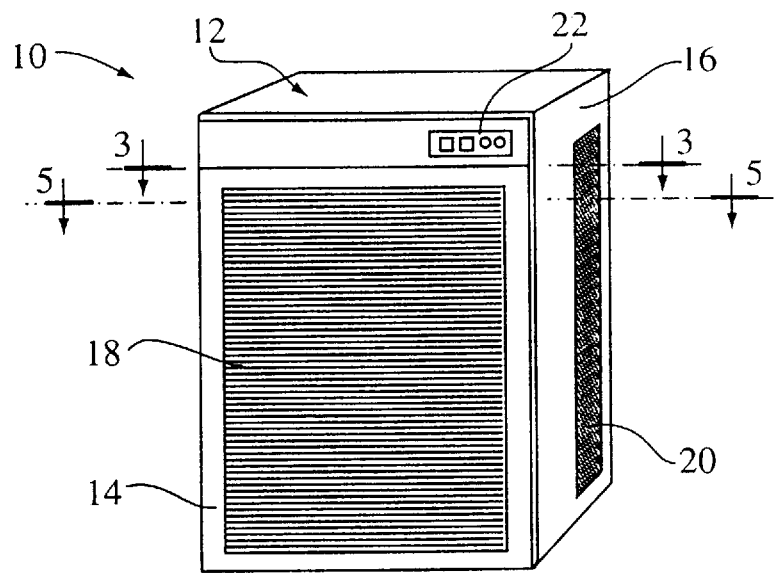
FIG. 1 is a perspective view of an exterior of the cabinet for a portable germicidal air filter in accordance with the invention.

FIG. 1 shows a perspective view of an exterior of a portable germicidal air filter generally indicated by the reference 10. The germicidal air filter 10 includes a cabinet 12 having a front wall 14 and opposed side walls 16. The front wall 14 includes an area for air intake 18 which may be louvred (as illustrated) or covered with a coarse open-celled plastic foam (not illustrated), or the like. The area for air intake permits air to be filtered to be drawn into the cabinet. The side walls 16 respectively include areas for air exhaust 20 which are preferably covered by a grid but may also be covered by louvres or the like. A top of the front wall 14 also includes a control panel 22 which will be explained in more detail with reference to FIG. 7.

Figure 2:
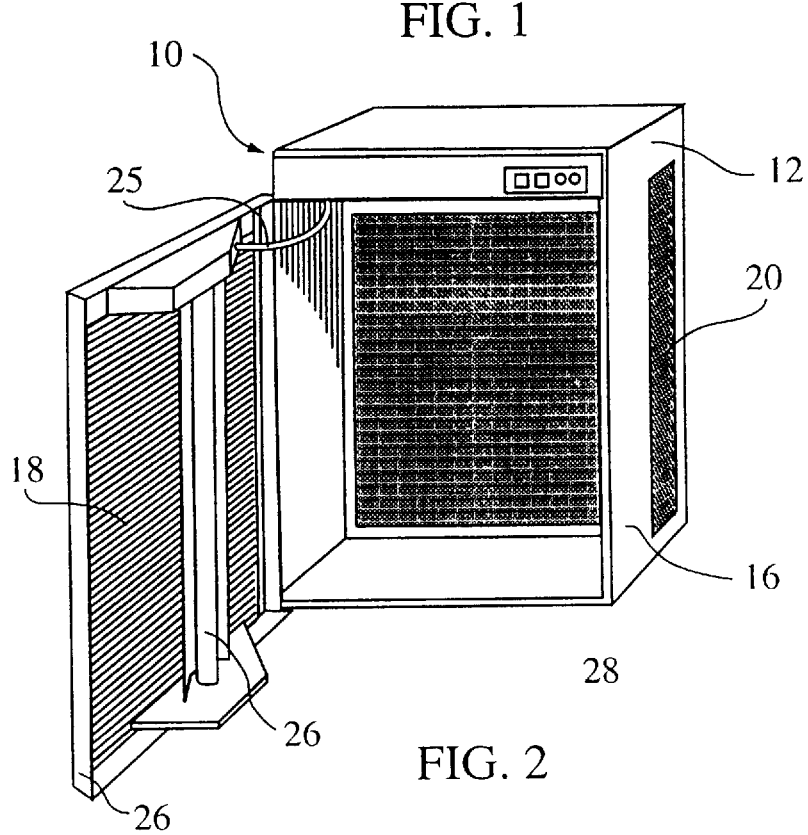
FIG. 2 is a perspective view of the cabinet shown in FIG. 1 with a service door open at the front of the unit showing the preferred position of the ultraviolet source and the filter medium.

FIG. 2 shows the germicidal air filter 10 with a service door 24 in an open condition. The service door forms a substantial part of the front wall 14 and is hinged to a side wall 16 so that it is conveniently opened to service the interior of the filter. Mounted to a centre of the service door 24 is an ultraviolet source 26, preferably an ultraviolet lamp. The ultraviolet lamp 26 may be an ozone generating lamp to facilitate and enhance the germicidal affect of the filter. Details of the mechanism for mounting the ultraviolet lamp 26 and focusing the ultraviolet radiation which it emits will be explained below with reference to FIGS. 3–6. Positioned between the service door 24 and the areas for air exhaust 20 is an air filter 28 the construction and operation of which is also explained below in more detail. An electrical power cable 25 supplies operating current to the ultraviolet lamp 26 and to an electric motor 38 (see FIG. 3) from an appropriate ballast and transformer (see FIG. 7) which are housed in a compartment (not illustrated) in the top of the cabinet 12.

Figure 3:
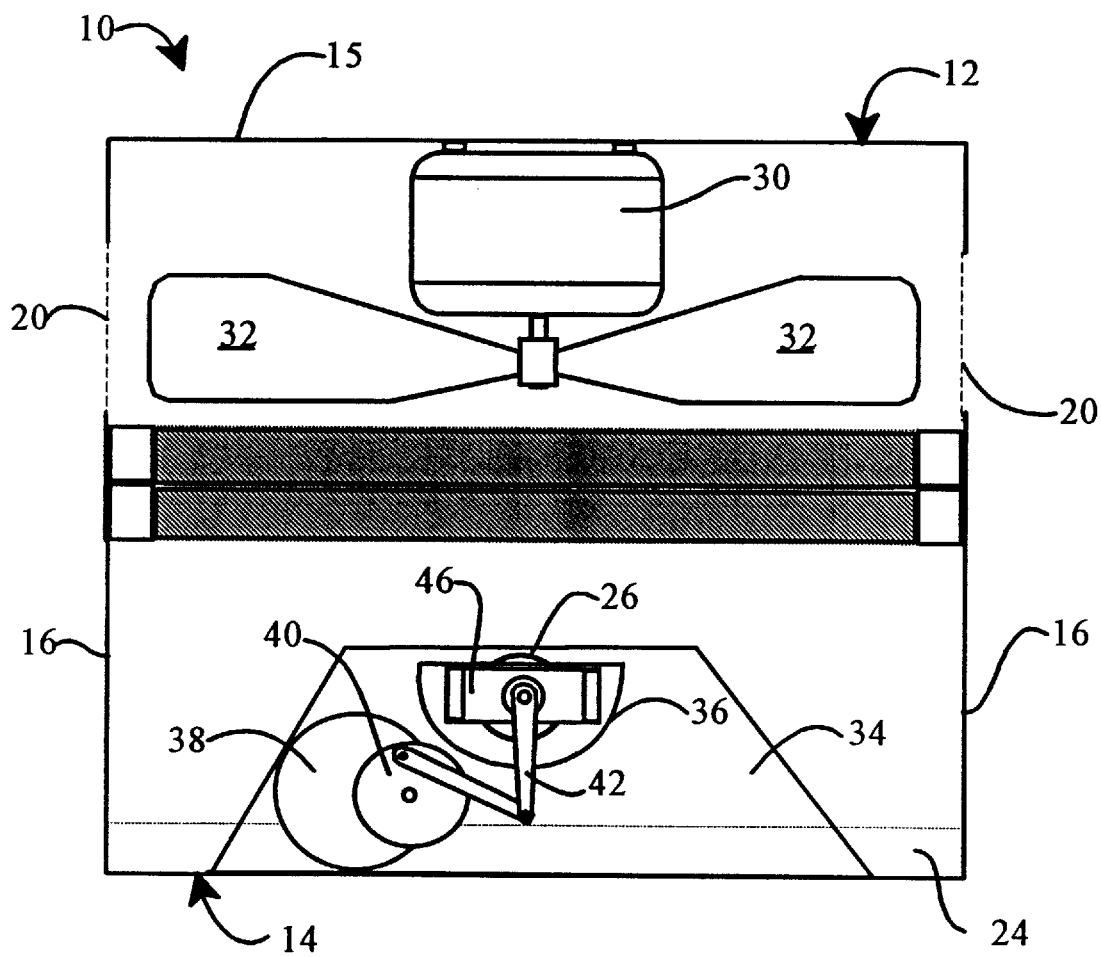
FIG. 3 is a top plan view taken along lines 3—3 of the portable germicidal air filter shown in FIG. 1.

FIG. 3 is a cross-sectional view of the cabinet 12 taken along lines 3—3 of FIG. 1. As is apparent, a fan consisting of fan motor 30 and fan blades 32 is mounted to a rear wall 15 of the cabinet 12. The fan blades 32 are set at a pitch, preferably 30°–40°, to draw air through the area for air intake in the front wall 14 of the cabinet 12 and expel the air through the areas for air exhaust 20 in the side walls 16 of the cabinet 12. The pitch of the fan blades is preferably in the range of 30°–40° because this pitch is most effective for moving air through the cabinet with least noise generation. At this pitch the fan blades impel air laterally through the areas for air exhaust 20 and the resulting vacuum draws air through the air intake 18. The air is thereby drawn through the air filter 28 which is preferably an electrostatic air filter of the charged media type well known in the art and described, for example, in U.S. Pat. No. 4,886,526 which issued Dec. 12, 1989 and is incorporated herein by reference. The air filter 28 is serviced by removing the filter from the cabinet 12 through the service door 24. After the air filter is removed from the cabinet 12, service is accomplished in a manner well known in the art and described for example in U.S. Pat. No. 4,886,526.

The only enhancements to the filter 28 described in that patent are several modifications to ensure that ultraviolet radiation is not reflected back out of the filter cabinet through the area for air intake 18 (see FIG. 1). To reduce reflection, the aluminum filter frame is painted matte black, as is the outer screen on the upstream side of the filter 28. In addition, the fibrous filter medium is preferably made from a glass fibre pad coloured black by the addition of carbon black to the glass mixture. Other colorants have proven to be unstable and transient when exposed to the ultraviolet radiation. The interior of the cabinet 12 between the service door 24 and the filter 28 (see FIG. 2) are likewise preferably painted matte black to reduce reflection.

A pair of support brackets 34 mount the ultraviolet lamp 26 to a center of the service door 24. Only the bottom bracket 34 is illustrated in FIG. 3 for clarity. When the service door 24 is in a closed condition, the distance from the ultraviolet lamp 26 to the upstream side of the filter 28 is preferably about 2.65" (6.73 cm). The upstream side of the filter medium is preferably about 10" (25.4 cm) wide and the cabinet is about 12" wide (30.48 cm). Given those dimensions, the distance from the ultraviolet lamp 26 to either outer edge of the upstream side of the filter 28 is about 5.88" (14.94 cm). A single ultraviolet lamp 26 is not adequate to irradiate the entire surface of the filter to germicidal levels. In order to conserve weight, manufacturing and maintenance expense, however, and ensure that unacceptable levels of radiation do not escape from the cabinet 12, it is preferable that the unit include only one ultraviolet lamp 26. A mechanism for focusing the radiation from the lamp onto a predefined area of the upstream side of the filter 28 is therefore desirable. The preferred mechanism for focusing the ultraviolet radiation is a parabolic reflector 36 which is oscillated about the lamp 26 to systematically sweep the focused radiation across the upstream side of the filter 28. Oscillation of the parabolic reflector is preferably accomplished by a 24 volt twin coil gear reduction motor 38 well known in the art which drives a fly wheel 40. The fly wheel 40 in turn moves a cam shaft assembly 42 having a first arm connected to the fly wheel 40 and a second arm connected to a shaft which supports the parabolic reflector 36 as will be explained in more detail with reference to FIG. 4.

Figure 4:
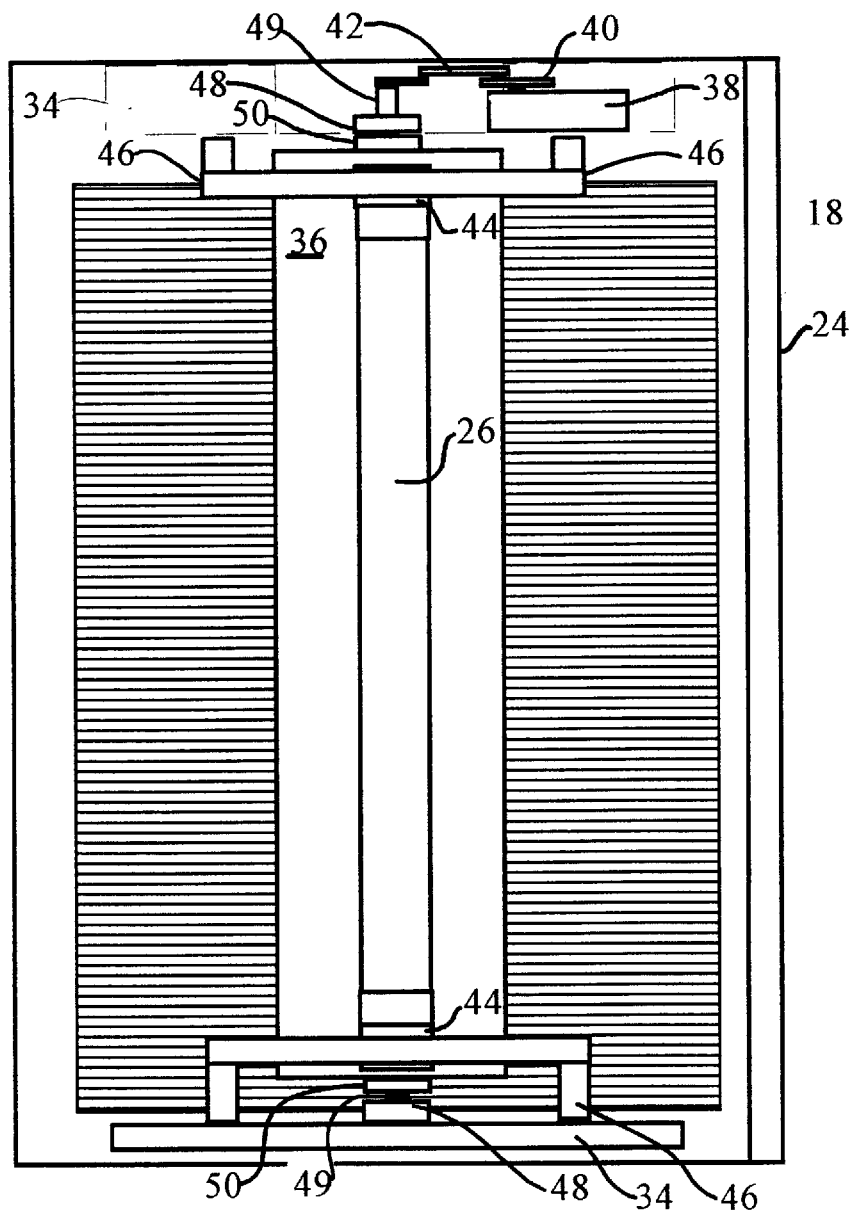
FIG. 4 is a schematic elevational view of the mechanism for oscillating a parabolic reflector or a lens for focusing the ultraviolet radiation emitted by an ultraviolet radiation source in the portable germicidal air filter shown in FIG. 1.

FIG. 4 shows an elevational view of the preferred mechanism for oscillating the parabolic reflector 36. The ultraviolet lamp 26 is preferably stationary and connected to lamp sockets 44. Each lamp socket 44 is supported by a U-shaped bracket 46 which is affixed to the respective support brackets 34 that are mounted to a centre of the inner side of the service door 24. Mounted under each U-shaped bracket 46 is a bearing 48 that accepts a stub shaft 49 which supports a reflector support bracket 50 attached to opposite ends of the parabolic reflector 36. At a top end of the reflector 36, a stub shaft 49 interconnects the reflector support bracket 50 with the cam shaft assembly 42 which is in turn connected to the fly wheel 40 of the gear reduction motor 38. As the gear reduction motor operates it rotates the fly wheel 40 preferably at about 2 revolutions per minute. The rotation of the fly wheel causes the cam shaft assembly 42 to oscillate the parabolic reflector 36 which sweeps focused radiation across the upstream side of the filter 28 as can be seen in FIGS. 5*a–c*.

Figure 5A:
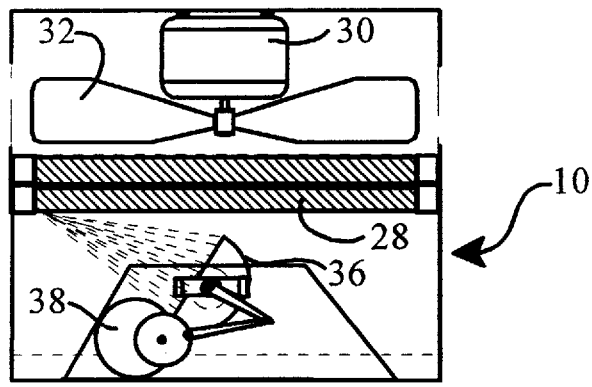
FIGS. 5a through 5c are cross-sectional views taken along lines 5—5 of the portable germicidal air filter shown in FIG. 1, to illustrate the way in which ultraviolet radiation is focused on an upstream side of the filter medium in the portable germicidal air filter.
Figure 5B:
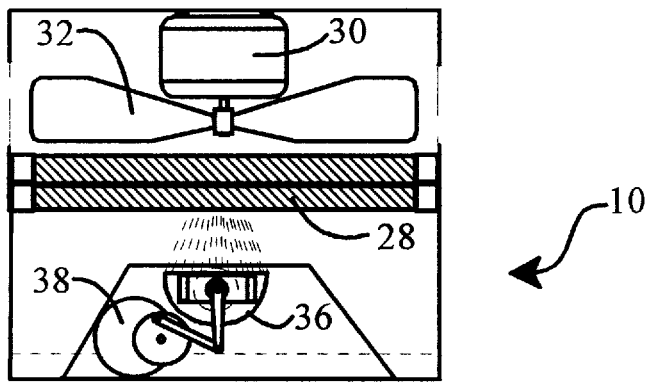
Figure 5C:
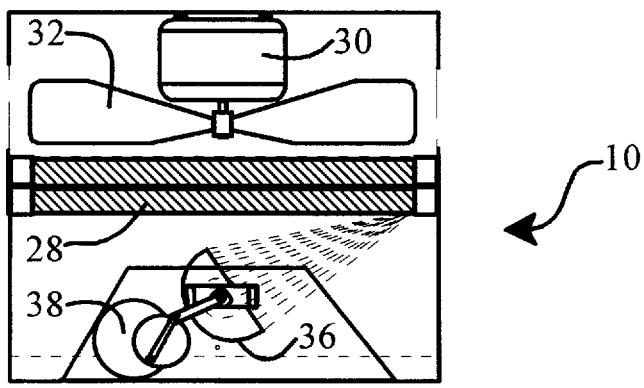

FIGS. 5*a–c* are cross-sectional views taken along lines 5—5 of FIG. 1. The parabolic reflector is preferably made from sheet metal of an aluminum alloy having a bright polished side to enhance reflection. Such sheet metal is available, for example, from Ideal Metal in Toronto, Canada and is identified as Aluminum Bright (1100-H24). The sheet metal is typically rolled into the desired shape using techniques well known in the art. The focal length of the parabolic reflector 36 is preferably such that the radiation emitted by the ultraviolet lamp 26 is most concentrated when the radiation is focused at the edges of the upstream side of the air filter 28 so that the germicidal affect on the upstream side of the air filter is as consistent as possible. In the preferred embodiment shown in FIGS. 5*a*–5*c*, the focal length of the parabolic reflector 36 is therefore preferably about 5.88" (14.94 cm). As the parabolic reflector 36 is oscillated so that the beam sweeps toward the centre of the filter (see FIG. 5*b*) it is apparent that the radiation is less focused on the upstream side of the filter medium 28, but since the strength of the radiation is inversely proportional to the distance from the source, the same germicidal effect is achieved over a greater area. Thus as the oscillation completes a sweep as shown in FIG. 5*c*, the radiation becomes more focused as the distance from the ultraviolet lamp increases, until the focus is most intense at the outer edge of the upstream face of the filter medium. It will be understood by those skilled in the art that the oscillation of the parabolic reflector 36 also has the beneficial effect of constantly changing the angle of incidence of the ultraviolet radiation on the upstream side of the air filter 28. This promotes deeper penetration of the radiation into the air filter medium and tends to eliminate shaded areas where bacteria, viruses or other airborne microorganisms may survive.

Figure 6:
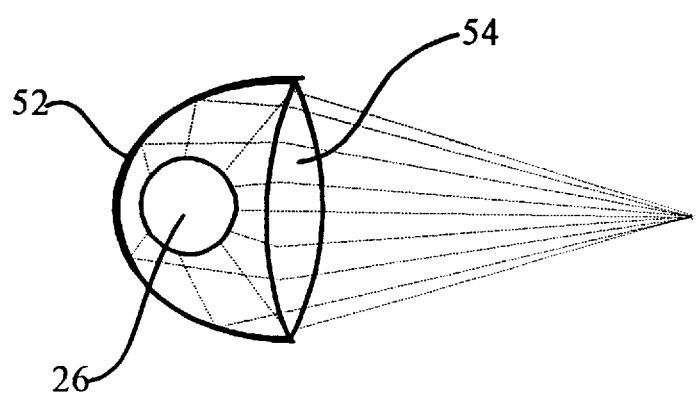
FIG. 6, which appears on sheet two of the drawings, shows an alternate arrangement for focusing the ultraviolet radiation in which a lens and reflector combination focus the radiation on the filter medium.

FIG. 6 shows an alternate arrangement for focusing the ultraviolet radiation emitted by the ultraviolet lamp 26. In this embodiment, a reflector 52, which is not a focused parabolic reflector, reflects ultraviolet radiation onto a convex lens 54 which focuses the ultraviolet radiation in much the same way as the parabolic reflector 36. The lens 54 is preferably a plastic lens made from, for example, acrylate (ROP-4) plastic available from Cyro Industries of Mount Arlington, N.J., U.S.A. Plastic is preferred for the lens 54 because it is light in weight and shatterproof. The acrylate plastic is preferred because it is resistant to the effects of the ultraviolet radiation and most of the ultraviolet radiation passes through it. The lens 54 is preferably designed to have a focal length such that the radiation emitted by the ultraviolet lamp 26 is most concentrated when the radiation is focused at the edges of the upstream side of the air filter 28. In the preferred embodiment shown in FIGS. 5*a*–5*c*, the focal length of the lens 54 is therefore preferably about 5.88" (14.94 cm). While it is obvious that the lens 54 protects the ultraviolet lamp 26 from exposure to dust particles suspended in the air to be filtered, it should be noted that the shape of the parabolic reflector 36 also protects the ultraviolet lamp 26 from exposure to dust particles suspended in the air to be filtered. As air is drawn around the reflector 34, the shape of the reflector creates a substantially static vacuum around the ultraviolet lamp 26, which inhibits dust particles suspended in the air to be filtered from coming into contact with the ultraviolet lamp and therefore tends to keep the lamp clean.

Figure 7:
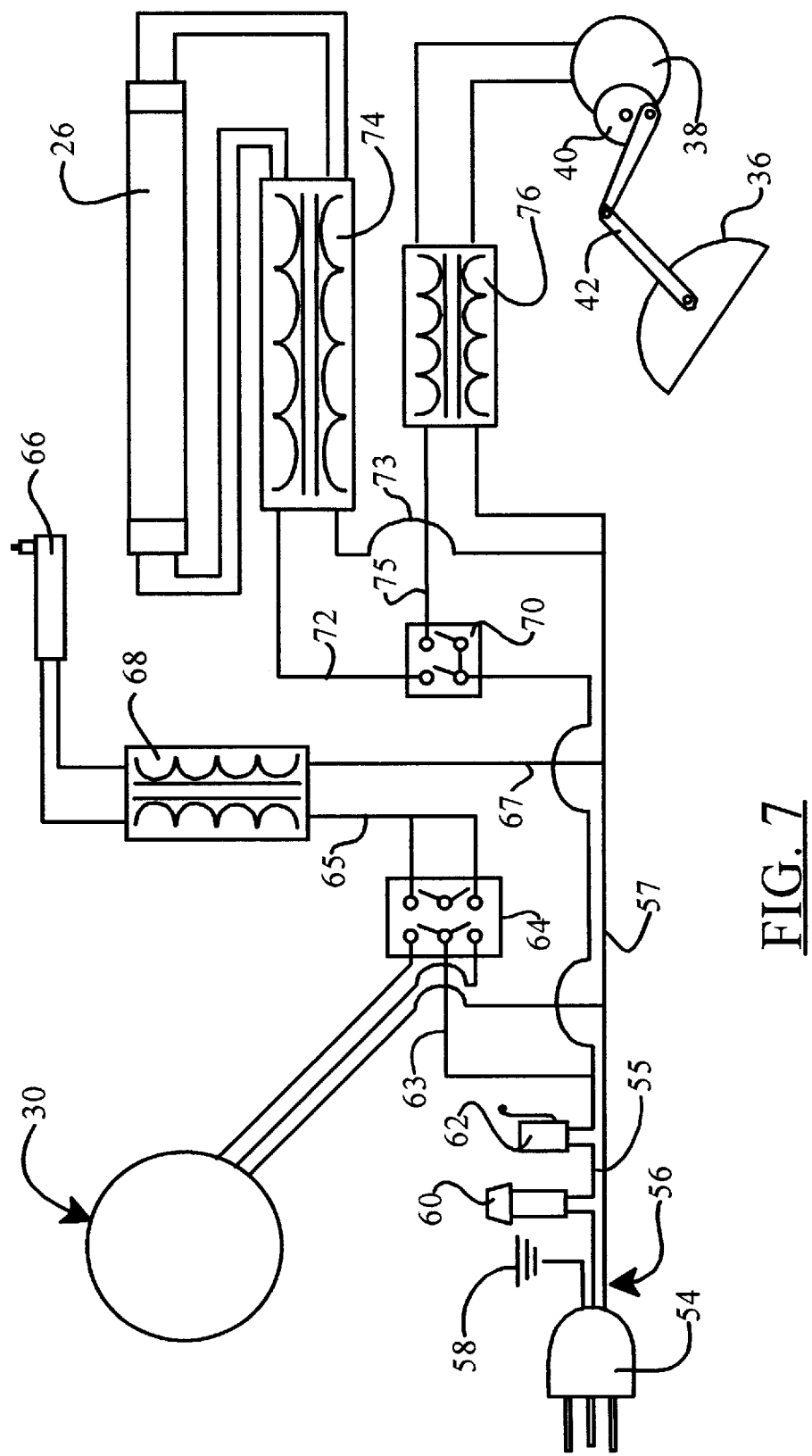
FIG. 7 is a wiring diagram suitable for a portable germicidal air filter in accordance with the invention.

FIG. 7 is a wiring diagram suitable for wiring the germicidal air filter 10 in accordance with the invention. A three prong power plug 54 is connected to a line cord 56 which typically supplies 120 VAC input current. A ground conductor of the line cord 56 is connected to ground 58 and a power conductor 55 of the line cord 56 is interrupted by a fuse 60 to protect the circuit from overload. An interlock switch 62 which is operatively associated with the service door 24 interrupts the power conductor 55 of the line cord 56 so that the unit is shut down whenever the service door 24 (see FIG. 2) is open in order to protect persons in the vicinity from exposure to ultraviolet radiation. A conductor 63 connects the power conductor 55 of line cord 56 to a dual speed fan motor switch 64 which is mounted to the control panel 22 (see FIG. 1). The dual speed fan motor switch 64 controls the operation of the fan motor 30 and supplies current to the high voltage electronics 66 which power the electrostatic air filter of the charged media type 28 in a manner well known in the art. Each pole of the dual speed fan switch 64 is connected to a conductor 65 for supplying current to a transformer 68. The return conductor of transformer 68 is connected to the return conductor 57 of the line cord 56 by a conductor 67. The high voltage electronics 66 require AC current which is output by the transformer 68. The power conductor 55 of the line cord 56 is likewise connected to a lamp and oscillating motor switch 70 which permits the ultraviolet radiation of the filter medium to be independently controlled from the operation of the fan and the electrostatic filter, if desired. The switch 70 is optional but is preferred so that the ultraviolet unit can be controlled without opening the service door 24 or disconnecting the line cord 56. Independent operation of the fan/filter and the ultraviolet lamp oscillator also permits the irradiation of the filter medium 28 to continue for a minute or two after the fan is shutdown, to ensure that any live microorganisms on the filter medium 28 are destroyed before the filter is serviced. This feature is important if the filter is used in an environment where antibiotic resistant microorganisms are known to be present.

A ballast 74 is connected to the lamp and oscillating motor switch 70 by a conductor 72, which is likewise connected by a conductor 73 to the return conductor of 57 of the line cord 56. The ballast 74 transforms the 120 volt AC input to a voltage suitable for driving the ultraviolet lamp 26. Also connected to the lamp and oscillating motor switch 70 by a conductor 75 is a transformer 76 which is also connected to the return conductor 57 of the line cord 56. The transformer 76 outputs a 24 volt AC current for driving the twin coil gear reduction motor 38. The transformer 68, the ballast 74 and the transformer 76 are preferably mounted to a bottom wall of a compartment (not illustrated) in cabinet 12 located above the filter 28 and behind the control panel 22 (see FIG. 2). It will be understood by those skilled in the art that this wiring diagram is exemplary only and other wiring arrangements may function equally well.

The efficiency of germicidal air filters has been tested in a 70 cubic foot test chamber filled with ambient air as described in U.S. Pat. No. 5,330,772 which is incorporated herein by reference. In that test, a petri dish containing agar agar was exposed to the air in the test chamber to collect a control sample of bacteria suspended in the air of the chamber prior to activation of a germicidal air filter installed in the test chamber. The temperature in the test chamber was 65° F. and the relative humidity was 50 percent at the time of testing. After the control sample was taken, the germicidal air filter was operated for a period of five minutes. The air flow through the filter was about 250 cubic feet per minute. After five minutes of operation, an identical petri dish containing agar agar was exposed to the air in the chamber using the same procedure used for the control sample, and both petri dishes were incubated to determine the bacteria containing particle counts before and after filtration. In the control sample about 65 bacteria-containing particles were collected. In the test sample taken after five minutes of operation, no bacteria-containing particles were collected. Insofar as the culture method was capable of testing for the presence of airborne bacteria, the test chamber was completely rid of such bacteria. It is therefore apparent that germicidal air filters are very effective in removing and destroying at least a portion of microorganisms suspended in air.

INDUSTRIAL APPLICABILITY

A simple, lightweight germicidal air filter suitable for home and/or personal use is provided. The filter removes at least a portion of the microorganisms suspended in the air filtered and destroys those microorganisms with ultraviolet radiation which is systematically focused at germicidal levels on an upstream side of the filter medium. Such air filters are known to be effective against microorganisms including bacteria, and microscopic insects such as dust mites and the like. The germicidal air filter in accordance with the invention therefore contributes to the comfort and safety of individuals, and provides a portable unit suitable for home and personal use that can be manufactured at an affordable price.

The construction of the preferred embodiment described above is intended to be exemplary only.

Although described with reference to portable electrostatic air filters, the invention is neither limited to portable applications, nor to electrostatically enhanced filter mediums. The invention may be adapted to permanent installations in air handling systems, or large wall or ceiling hung filtration units. It may also be adapted for use with passive filter mediums.

Variations, modifications and alterations may be apparent to those skilled in the art. The scope of the invention is intended to be limited only by the scope of the appended claims.

I claim:

1. A germicidal air filter, comprising:
   a stationary filter medium for removing particulate matter including at least a portion of microorganisms from an air stream to be filtered, the filter medium having an upstream side exposed to the air to be filtered;
   at least one ultraviolet radiation source located in proximity of the upstream side of the filter medium for exposing at least a portion of that side of the filter medium to ultraviolet radiation;
   means for focusing the ultraviolet radiation emitted by the source so that a predefined area of the upstream side of the filter medium is exposed to the focused ultraviolet radiation at any given time; and
   means for oscillating the means for focusing the ultraviolet radiation so that a surface of the upstream side of the filter medium is systematically exposed to germicidal levels of radiation.

2. A germicidal air filter as claimed in claim 1, wherein the means for focusing the ultraviolet radiation emitted by the source comprises a parabolic reflector which focuses the ultraviolet radiation in an elongated narrow band on the filter medium.

3. A germicidal air filter as claimed in claim 2, wherein the means for oscillating the parabolic reflector is a gear reduction motor and a cam assembly for oscillating the reflector about an axis so that the upstream side of the filter medium is systematically exposed to focused ultraviolet radiation.

4. A germicidal air filter as claimed in claim 1, wherein the means for focusing the ultraviolet radiation is a reflector and an elongated lens which focuses the ultraviolet radiation in an elongated narrow band on the filter medium.

5. A germicidal air filter as claimed in claim 4, wherein the means for oscillating the reflector and the elongated lens is a gear reduction motor and a cam assembly for oscillating the lens about an axis so that the upstream side of the filter medium is systematically exposed to focused ultraviolet radiation.

6. A germicidal air filter as claimed in claim 1 wherein the filter medium is a fibrous filter medium.

7. The germicidal air filter as claimed in claim 6, wherein the fibrous filter medium is electrostatically enhanced so that the fibres of the filter are polarized by an electrostatic field to increase the efficiency of the filter medium in capturing particulate matter suspended in air to be filtered.

8. The germicidal air filter as claimed in claim 7, wherein the filter medium is a pleated paper medium suitable for use in filtering air.

9. The germicidal air filter as claimed in claim 7, wherein the filter medium is a fibreglass medium suitable for use in filtering air.

10. The germicidal air filter as claimed in claim 1, wherein the ultraviolet radiation source is an ultraviolet lamp.

11. The germicidal air filter as claimed in claim 10, wherein the ultraviolet lamp is an ozone producing lamp.

12. A germicidal air purifier comprising:
   a cabinet having at least one area for admitting air to be filtered and at least one area for exhausting filtered air from the cabinet;
   a planar filter medium arranged in the cabinet so that substantially all of the air to be filtered passes through the filter medium, the filter medium having an upstream side and a downstream side;
   means for moving air to be filtered through the at least one area for admitting air to be filtered, the filter medium and the at least one area for exhausting filtered air; and
   an ultraviolet lamp mounted adjacent the upstream side of the filter medium;
   means for focusing the ultraviolet radiation emitted by the lamp so that a predefined area of the upstream side of the filter medium is exposed to the focused ultraviolet radiation at any given time;
   means for oscillating the means for focusing the ultraviolet radiation so that at least a substantial portion of a surface of the upstream side of the filter medium is systematically exposed to germicidal levels of radiation;
   whereby airborne microorganisms suspended in air to be filtered are captured on the upstream side of the filter medium and exposed to a lethal dose of radiation when the oscillation of the means for focusing the ultraviolet radiation moves the focused radiation onto the captured microorganisms.

13. A germicidal air purifier as claimed in claim 12, wherein the at least one area for admitting air to be filtered comprises a service access door having a front panel that is louvred for admitting air.

14. A germicidal air purifier as claimed in claim 12, wherein the at least one area for exhausting filtered air from the cabinet comprises a grid in each sidewall of the cabinet.

15. A germicidal air purifier as claimed in claim 12, wherein the filter medium is an electrostatically enhanced fibrous filter medium.

16. A germicidal air purifier as claimed in claim 15, wherein the fibrous filter medium is a fibreglass impregnated with carbon black to minimize the reflection of ultraviolet radiation from the upstream side of the filter medium.

17. a germicidal air purifier as claimed in claim 16, wherein the upstream side of the filter medium includes a frame that surrounds the filter medium and a charging screen attached to the frame that covers the fibrous filter medium, and the frame and the charging screen are painted matte black to reduce reflection of the ultraviolet radiation.

18. A germicidal air purifier as claimed in claim 17, wherein an interior of the cabinet upstream of the filter medium is painted matte black to minimize reflection of the ultraviolet radiation.

19. A germicidal air purifier as claimed in claim 12, wherein the means for focusing the ultraviolet radiation is a parabolic reflector.

20. A germicidal air purifier as claimed in claim 19, wherein the parabolic reflector is made from sheet aluminum having a polished side positioned next to the ultraviolet lamp.

21. A germicidal air purifier as claimed in claim 20, wherein the means for oscillating the parabolic reflector is a gear reduction motor which drives a cam assembly.

22. A germicidal air purifier as claimed in claim 20, wherein the gear reduction motor rotates at about 2 rpm.

23. A germicidal air purifier as claimed in claim 12, wherein the means for moving air to be filtered is a fan attached to a rear wall of the cabinet.

24. A germicidal air purifier as claimed in claim 23, wherein the fan has blades with 30°–40° of pitch.

* * * * *